United States Patent
McNeel et al.

(10) Patent No.: US 6,380,182 B1
(45) Date of Patent: Apr. 30, 2002

(54) METHODS AND COMPOSITIONS CONTROLLING BIOFOULING USING SULFAMIC ACIDS

(76) Inventors: Thomas E. McNeel; Marilyn S. Whittemore; Stephen D. Bryant; Graciela H. Vunk, all c/o Buckman Laboratories International, Inc., 1256 N. McLean Blvd., Memphis, TN (US) 38108

( * ) Notice: Subject to any disclaimer, the term of this patent is extended or adjusted under 35 U.S.C. 154(b) by 0 days.

(21) Appl. No.: 09/575,665

(22) Filed: Jun. 12, 2000

Related U.S. Application Data

(62) Division of application No. 08/901,895, filed on Jul. 29, 1997, now Pat. No. 6,103,131.

(51) Int. Cl.[7] ............... A61K 31/55; A01N 59/00; C07D 225/00; C07D 265/00; C07D 211/36

(52) U.S. Cl. ............... 514/211.01; 514/212.01; 514/230.8; 514/231.2; 514/247; 514/256; 514/315; 514/359; 514/374; 514/378; 514/398; 514/408; 514/424; 514/608; 548/215; 548/240; 548/300.1; 504/150; 504/154; 504/155; 504/156; 540/450; 540/484; 544/63; 544/106; 544/239; 544/242; 544/336; 546/242

(58) Field of Search ............... 514/211.01, 212.01, 514/230.8, 231.2, 247, 256, 315, 359, 374, 378, 398, 408, 424, 608; 504/150, 154, 155, 156; 540/450, 484; 544/63, 106, 239, 242, 336; 546/242; 548/215, 240, 300.1

(56) References Cited

U.S. PATENT DOCUMENTS

| | | | |
|---|---|---|---|
| 3,637,679 A | 1/1972 | Lovell et al. | 260/243 |
| 3,705,989 A | 12/1972 | Oshima et al. | 424/256 |
| 4,293,559 A | 10/1981 | Buckman et al. | 424/270 |
| 4,295,932 A | 10/1981 | Pocius | 162/161 |
| 5,250,194 A | 10/1993 | Hollis et al. | 210/764 |
| 5,464,636 A | 11/1995 | Hight et al. | 424/661 |
| 5,814,668 A | 9/1998 | Whittemore et al. | 514/625 |
| 5,888,405 A | 3/1999 | McNeel et al. | 210/764 |
| 5,902,808 A | 5/1999 | Whittemore et al. | 514/231.2 |

FOREIGN PATENT DOCUMENTS

| | | |
|---|---|---|
| GB | 1 301 861 | 1/1973 |
| GB | 2 163 348 | 2/1986 |
| WO | 97/11913 | 4/1997 |

OTHER PUBLICATIONS

Delaquis et al., "Detachment Of *Pseudomonas fluorescens* From Biofilms On Glass Surfaces In Response To Nutrient Stress," Microb. Ecol. vol. 18, pp. 199–210 (1989).

Fletcher et al., "Influence Of Substratum Characteristics On The Attachment Of A Marine Pseudomonad To Solid Surfaces" Appl. Environ. Microbiol. vol. 37, pp. 67–72 (1979).

Humphries et al., "The Effect Of A Range Biological Polymers And Synthetic Surfactants On the Adhesion Of A Marine Pseudomonas sp. Strain NCMB 2021 To Hydrophilic And Hydrophobic Surfaces" FEMS Microbiol. Ecol. vol. 38, pp. 299–308 (1986).

Beilsteins Handbuch der Organischen Chemie, vol. 20, 4EW, p. 1158 (1978).

Humphries et al., "The Use of Non–Ionic Ethoxylated And Propoxylated Surfactants To Prevent The Adhesion Of Bacteria To Solid Surfaces" FEMS Microbiology Letters vol. 42, pp. 91–101 (1987).

Kent, in "Biological Fouling: Basic Science and Models" (in Melo, L.F., Bott, T.R. Bernardo, C.A. (Eds.), Fouling Science and Technology, NATO ASI Series, Series E, Applied Sciences: No. 145, Kluwer Acad. Publishers, Dordrecht, The Nederlands 1988).

Nickless, G., Inorganic Sulphur Chemistry, Elsevier Publishing Company, New York (eds.), pp. 611–614 (1968).

*Primary Examiner*—Richard L. Raymond
*Assistant Examiner*—Tamthom N. Truong
(74) *Attorney, Agent, or Firm*—Morgan, Lewis & Bockius LLP

(57) ABSTRACT

The invention relates to a method to inhibit bacteria from adhering to a submergible surface. The method contacts the submergible surface with an effective amount of at least one sulfamic acid or salt thereof to inhibit bacterial adhesion to the submergible surface. The invention also relates to a method for controlling biofouling of an aqueous system. This method adds an effective amount of at least one sulfamic acid or salt thereof to inhibit bacteria from adhering to a submerged surface within the aqueous system. This method effectively controls biofouling without substantially killing the fouling organisms. The sulfamic acid used in the method of the invention has the formula $R^1R^2NS(O)_2(OH)$. In this formula, R1 and R2 are independently a hydrogen, a $C_4$–$C_{20}$ alkyl group or a cyclohexyl group. However, $R^1$ and $R^2$ are not both hydrogen. Alternatively, $R^1$ and $R^2$, together with the N, may also form a 5–8 membered heterocyclic ring having the formula:

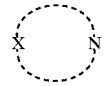

In the heterocyclic ring, X is O, NH, or $CH_2$. The salt of sulfamic acid can be an acid salt or quaternized sulfamic acid salt. The present invention also relates to a composition containing sulfamic acids or salts thereof useable in the above methods. The compositions comprise at least one sulfamic acid or salt thereof in an amount effective to inhibit bacteria from adhering to submergible or submerged surfaces.

17 Claims, No Drawings

METHODS AND COMPOSITIONS CONTROLLING BIOFOULING USING SULFAMIC ACIDS

CROSS-REFERENCE TO RELATED APPLICATIONS

Referenced-applications

This application is a division of U.S. patent application Ser. No. 08/901,895, filed Jul. 29, 1997, now U.S. Pat. No. 6,103,131, the disclosure of which is herein incorporated by reference.

STATEMENT REGARDING FEDERALLY SPONSORED RESEARCH

Not Applicable

REFERENCE TO A MICROFICHE APPENDIX

Not Applicable

BACKGROUND OF THE INVENTION

1. Description of Related Art

Microorganisms adhere to a wide variety of surfaces, particularly surfaces in contact with aqueous fluids which provide a suitable environment for microbial growth. For example, microorganisms are known to adhere to ship hulls, marine structures, teeth, medical implants, cooling towers, and heat exchangers. Adhering to such submerged or submergible surfaces, microorganisms may foul the surface or cause it to deteriorate.

In mammals, (e.g., humans, livestock, pets), microorganisms adhered to a surface may lead to health problems. Plaque, for example, results from microorganisms adhering to the surfaces of teeth. Medical implants with unwanted microorganisms adhered to their surfaces often become crusted over and must be replaced.

Scientific studies have shown that the first stage of biofouling in aqueous systems is generally the formation of a thin biofilm on submerged or submergible surfaces, i.e., surfaces exposed to the aqueous system. Attaching to and colonizing on a submerged surface, microorganisms such as bacteria, are generally thought to form the biofilm and modify the surface to favor the development of the more complex community of organisms that make up the advanced biofouling of the aqueous system and its submerged surfaces. A general review of the mechanisms of the importance of biofilm as the initial stage in biofouling is given by C. A. Kent in "Biological Fouling: Basic Science and Models" (in Melo, L. F., Bott, T. R., Bernardo, C. A. (eds.), Fouling Science and Technology, NATO ASI Series, Series E, Applied Sciences: No. 145, Kluwer Acad. Publishers, Dordrecht, The Netherlands, 1988). Other literature references include M. Fletcher and G. I. Loeb, Appl. Environ. Microbiol. 37 (1979) 67–72; M. Humphries et al., FEMS Microbiology Ecology 38 (1986) 299–308; and M. Humphries et. al., FEMS Microbiology Letters 42 (1987) 91–101.

Biofouling, or biological fouling, is a persistent nuisance or problem in a wide variety of aqueous systems. Biofouling, both microbiological and macrobiological fouling, is caused by the buildup of microorganisms, macroorganisms, extracellular substances, and dirt and debris that become trapped in the biomass. The organisms involved include microorganisms such as bacteria, fungi, yeasts, algae, diatoms, protozoa, and macroorganisms such as macroalgae, barnacles, and small mollusks like Asiatic clams or Zebra Mussels.

Another objectionable biofouling phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and have a characteristic, undesirable odor that is different from that of the aqueous system in which it formed. The microorganisms involved in slime formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms.

Biofouling, which often degrades an aqueous system, may manifest itself as a variety of problems, such as loss of viscosity, gas formation, objectionable odors, decreased pH, color change, and gelling. Additionally, degradation of an aqueous system can cause fouling of the related water-handling system, which may include, for example, cooling towers, pumps, heat exchangers, and pipelines, heating systems, scrubbing systems, and other similar systems.

Biofouling can have a direct adverse economic impact when it occurs in industrial process waters, for example in cooling waters, metal working fluids, or other recirculating water systems such as those used in papermaking or textile manufacture. If not controlled, biological fouling of industrial process waters can interfere with process operations, lowering process efficiency, wasting energy, plugging the water-handling system, and even degrade product quality.

For example, cooling water systems used in power plants, refineries, chemical plants, air-conditioning systems, and other industrial operations frequently encounter biofouling problems. Airborne organisms entrained from cooling towers as well as waterborne organisms from the system's water supply commonly contaminate these aqueous systems. The water in such systems generally provides an excellent growth medium for these organisms. Aerobic and heliotropic organisms flourish in the towers. Other organisms grow in and colonize such areas as the tower sump, pipelines, heat exchangers, etc. If not controlled, the resulting biofouling can plug the towers, block pipelines, and coat heat-transfer surfaces with layers of slime and other biologic mats. This prevents proper operation, reduces cooling efficiency and, perhaps more importantly, increases the costs of the overall process.

Industrial processes subject to biofouling also include papermaking, the manufacture of pulp, paper, paperboard, etc. and textile manufacture, particularly water-laid non-woven textiles. These industrial processes generally recirculate large amounts of water under conditions which favor the growth of biofouling organisms.

Paper machines, for example, handle very large volumes of water in recirculating systems called "white water systems." The furnish to a paper machine typically contains only about 0.5% of fibrous and non-fibrous papermaking solids, which means that for each ton of paper almost 200 tons of water pass through the headbox. Most of this water recirculates in the white water system. White water systems provide excellent growth media for biofouling microorganisms. That growth can result in the formation of slime and other deposits in headboxes, waterlines, and papermaking equipment. Such biofouling not only can interfere with water and stock flows, but when loose, can cause spots, holes, and bad odors in the paper as well as web breaks—costly disruptions in paper machine operations.

Biofouling of recreational waters such as pools or spas or decorative waters such as ponds or fountains can severely detract from people's enjoyment of them. Biological fouling often results in objectional odors. More importantly, particularly in recreational waters, biofouling can degrade the water quality to such an extent that it becomes unfit for use and may even pose a health risk.

Sanitation waters, like industrial process waters and recreational waters, are also vulnerable to biofouling and its associated problems. Sanitation waters include toilet water, cistern water, septic water, and sewage treatment waters. Due to the nature of the waste contained in sanitation waters, these water systems are particularly susceptible to biofouling.

To control biofouling, the art has traditionally treated an affected water system with chemicals (biocides) in concentrations sufficient to kill or greatly inhibit the growth of biofouling organisms. See, e.g., U.S. Pat. Nos. 4,293,559 and 4,295,932. For example, chlorine gas and hypochlorite solutions made with the gas have long been added to water systems to kill or inhibit the growth of bacteria, fungi, algae, and other troublesome organisms. However, chlorine compounds may not only damage materials used for the construction of aqueous systems, they may also react with organics to form undesirable substances in effluent streams, such as carcinogenic chloromethanes and chlorinated dioxins. Certain organic compounds, such as methylenebisthiocyanate, dithiocarbamates, haloorganics, and quaternary ammonium surfactants, have also been used. While many of these are quite efficient in killing microorganisms or inhibiting their growth, they may also be toxic or harmful to humans, animals, or other non-target organisms.

One possible way to control the biofouling of aqueous systems, which include the associated submerged surfaces, would be to prevent or inhibit bacterial adhesion to submerged surfaces within the aqueous system. This can be done, of course, using microbicides which, however, generally suffer from some of the disadvantages mentioned above. As an alternative, the present invention provides methods and compositions useful to substantially inhibit bacterial adhesion to a submerged or submergible surface and in controlling biofouling of aqueous systems. The invention obviates the disadvantages of prior methods. Other advantages of this invention will become apparent from a reading of the specifications and appended claims.

2. Field of the Invention

The invention uses a sulfamic acid or a salt thereof to inhibit bacterial adhesions to submergible or submerged surfaces, particularly those surfaces within an aqueous system. The invention also relates to methods and compositions for controlling biological fouling.

BRIEF SUMMARY OF THE INVENTION

The invention relates to a method to inhibit bacteria from adhering to a submergible surface. The method contacts the submergible surface with an effective amount of at least one sulfamic acid or a salt thereof to inhibit bacteria from adhering to a submergible surface. The sulfamic acid used in the method has the following formula $R^1R^2NS(O)_2(OH)$. In this formula, $R^1$ and $R^2$ are, independently, a hydrogen, a $C_4$–$C_{20}$ alkyl group or a cyclohexyl group. However, $R^1$ and $R^2$ are not both hydrogen. Alternatively, $R^1$ and $R^2$ together with the N may also form a 5–8 membered heterocyclic ring having the formula:

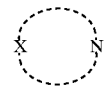

In the heterocyclic ring, X is O, NH, or $CH_2$. The dashed lines indicate that the group X may occupy different positions in a particular heterocyclic ring.

The invention relates also to a method for controlling biofouling of an aqueous system.

This method adds to an aqueous system an effective amount of at least one sulfamic acid, described above, or salt thereof to inhibit bacteria from adhering to submerged surfaces within the aqueous system. This method effectively controls biofouling without substantially killing the bacteria.

The invention also relates to a composition for controlling biofouling of an aqueous system. The composition comprises at least one sulfamic acid or a salt thereof in an amount effective to inhibit bacteria from adhering to a submergible surface or a submerged surface within the aqueous system.

BRIEF DESCRIPTION OF THE SEVERAL VIEWS OF THE DRAWINGS

Not Applicable

DETAILED DESCRIPTION OF THE INVENTION

In one embodiment, this invention relates to a method to inhibit bacteria from adhering to a submergible surface. A submergible surface is one which may be at least partially covered, overflowed, or wetted with a liquid such as water or another aqueous fluid or liquid. The surface may be intermittently or continually in contact with the liquid. As discussed above, examples of submergible surfaces include, but are not limited to ship or boat hulls, marine structures, teeth, medical implants, surfaces within an aqueous system such as the inside of a pump, pipe, cooling tower, or heat exchanger. A submergible surface may be composed of hydrophobic, hydrophilic, or metallic materials. Advantageously, using a sulfamic acid or salt thereof according to the invention can effectively inhibit bacteria from adhering to hydrophobic, hydrophilic, or metallic submergible or submerged surfaces.

To inhibit the adhesion of a bacteria to a submergible surface, the method contacts the submergible surface with a sulfamic acid or salt thereof. The surface is contacted with an effective amount of a sulfamic acid or salt thereof, or mixture of sulfamic acids or salts thereof, to inhibit microorganism adhesion to the surface. Preferably, a sulfamic acid or its salt is applied as a pretreatment of the submergible surface prior to submerging in an aqueous system. The sulfamic acid or salt thereof may be applied to the submergible surface using means known in the art. For example, as discussed below, the sulfamic acid or salt thereof may be applied by spraying, coating or dipping the surface with a liquid formulation containing the sulfamic acid or salt thereof. Alternatively, the sulfamic acid or salt thereof may be formulated in a paste which is then spread or brushed on the submergible surface. Advantageously, the sulfamic acid or salt thereof may be a component of a composition or formulation commonly used with a particular submergible surface.

"Inhibiting bacteria from adhering" to a submergible surface means to allow a scant or insignificant amount of bacterial adhesion for a desired period of time. Preferably, essentially no bacterial adhesion occurs and more preferably, it is prevented. The amount of sulfamic acid or salt thereof employed should allow only scant or insignificant bacterial adhesion and may be determined by routine testing. Preferably, the amount of sulfamic acid or salt thereof used is sufficient to apply at least a monomolecular film of sulfamic acid or salt thereof to the submergible surface. Such a film preferably covers the entire submergible surface.

Contacting a submergible surface with a sulfamic acid or salt thereof according to this method allows the surface to be pretreated against bacterial adhesion. Accordingly, the surface may be contacted with a sulfamic acid or salt thereof then submerged in the aqueous system.

The present invention relates also to a method for controlling biofouling of an aqueous system. An aqueous system comprises not only the aqueous fluid or liquid flowing through the system but also the submerged surfaces associated with the system. Submerged surfaces are those surfaces in contact with the aqueous fluid or liquid. Like the submergible surfaces discussed above, submerged surfaces include, but are not limited to, the inside surfaces of pipes or pumps, the walls of a cooling tower or headbox, heat exchangers, screens, etc. In short, surfaces in contact with the aqueous fluid or liquid are submerged surfaces and are considered part of the aqueous system.

The method of the invention adds at least one sulfamic acid or salt thereof to the aqueous system in an amount which effectively inhibits bacteria from adhering to a submerged surface within the aqueous system. At the concentration used, this method effectively controls biofouling of the aqueous system without substantially killing the bacteria.

"Controlling biofouling" of the aqueous system means to control the amount or extent of biofouling at or below a desired level and for a desired period of time for the particular system. This can eliminate biofouling from the aqueous system, reduce the biofouling to a desired level, or prevent biofouling entirely or above a desired level.

According to the present invention, "inhibiting bacteria from adhering" to a submerged surface within the aqueous system means to allow a scant or insignificant amount of bacterial adhesion for a desired period of time for the particular system. Preferably, essentially no bacterial adhesion occurs and more preferably, bacterial adhesion is prevented. Using a sulfamic acid or salt thereof according to the invention can, in many cases, break up or reduce other existing attached microorganisms to undetectable limits and maintain that level for a significant period of time.

While some sulfamic acids or salts thereof may exhibit biocidal activity at concentrations above certain threshold levels, sulfamic acids or salts thereof effectively inhibit bacterial adhesion at concentrations generally well below such threshold levels. According to the invention, the sulfamic acid or salt thereof inhibits bacterial adhesion without substantially killing the bacteria. Thus, the effective amount of a sulfamic acid or salt thereof used according to the invention is below its toxic threshold, if the sulfamic acid or salt thereof also has biocidal properties. For example, the concentration of the sulfamic acid or salt thereof may be ten or more times below its toxic threshold. Preferably, the sulfamic acid or salt thereof should also not harm non-target organisms which may be present in the aqueous system.

A sulfamic acid or salt thereof, or a mixture of sulfamic acids or salts thereof, may be used to control biofouling in a wide variety of aqueous systems such as those discussed above. These aqueous systems include, but are not limited to, industrial aqueous systems, sanitation aqueous systems, and recreational aqueous systems. As discussed above, examples of industrial aqueous systems are metal working fluids, cooling waters (e.g., intake cooling water, effluent cooling water, and recirculating cooling water), and other recirculating water systems such as those used in papermaking or textile manufacture. Sanitation aqueous systems include waste water systems (e.g., industrial, private, and municipal waste water systems), toilets, and water treatment systems, (e.g., sewage treatment systems). Swimming pools, fountains, decorative or ornamental pools, ponds or streams, etc., provide examples of recreational water systems.

The effective amount of a sulfamic acid or salt thereof to inhibit bacteria from adhering to a submerged surface in a particular system will vary somewhat depending on the aqueous system to be protected, the conditions for microbial growth, the extent of any existing biofouling, and the degree of biofouling control desired. For a particular application, the amount of choice may be determined by routine testing of various amounts prior to treatment of the entire affected system. In general, an effective amount used in an aqueous system may range from about 1 to about 500 parts per million and more preferably from about 20 to about 100 parts per million of the aqueous system.

The sulfamic acids or salts thereof employed in the present invention have the following general formula $R^1R^2NS(O)_2(OH)$. In this formula, $R^1$ and $R^2$ are, independently, a hydrogen, a $C_4$–$C_{20}$ alkyl group or a cyclohexyl group. But, $R^1$ and $R^2$ are not both hydrogen.

Preferably, $R^1$ is a $C_5$–$C_{20}$ alkyl group and $R^2$ is a hydrogen. When $R^1$ and $R^2$ is an alkyl group, it is preferably a $C_8$–$C_{18}$ alkyl group, more preferably, a $C_{10}$–$C_{14}$ alkyl group, and most preferably a $C_{12}$ alkyl group. The alkyl group may be bound through a terminal carbon or a carbon in the alkyl chain. The alkyl group may contain carbon-carbon double or triple bonds and may also be branched or unbranched.

Alternatively, $R_1$ and $R_2$ together with the N may also form a 5–8 membered heterocyclic ring having the formula:

In the heterocyclic ring, X is O, NH, or $CH_2$. The dashed lines indicate that the group X may occupy different positions in a particular heterocyclic ring. Preferably, the heterocyclic ring is 5- or 6-membered ring. Specific preferred rings include morpholinyl and piperidinyl.

Specific preferred sulfamic acids of the above formula include butyl sulfamic acid, compound (a); amyl sulfamic acid, compound (b); octyl sulfamic acid, compound (c); dioctyl sulfamic acid, compound (d); dodecyl sulfamic acid, compound (e); didodecyl sulfamic acid, compound (f); octadecyl sulfamic acid, compound (g); dicyclohexyl sulfamic acid, compound (h); morpholino sulfamic acid, compound (i); and piperidinyl sulfamic acid, compound (j).

Sulfamic acids or salts thereof useful in the invention are available either commercially from chemical supply houses or may be prepared from starting materials using well-known literature methods. For example, a sulfamic acid or salt thereof may be prepared by the following method. An amine is dissolved in a dry solvent, such as THF, and chilled in an ice bath. An acid, such as chlorosulfonic acid, is added dropwise to the amine in an equimolar amount, i.e. 1 mol of acid per 1 mol of amine. After the reaction is complete, the solvent was removed by rotary evaporation. The sulfamic acid or salt thereof is collected by filtration and washed with water. Methods for the preparation of various sulfamic acids or salts thereof are described in Nickless, G. Inorganic Sulphur Chemistry, Elsevier Publishing Company, New York; 611–614 (1968).

Salts of sulfamic acids can also be used in the invention. Sulfamic acids are amphoteric, i.e. exhibit both acidic and basic properties. Accordingly, two types of sulfamic acid salts can be formed: a salt of the acid moiety and a salt of the basic or nitrogen moiety. Salts of the acid moiety (referred to as "acid salts") include, but are not limited to, alkali metal and quaternary ammonium salts. Salts of the basic or nitrogen moiety (referred to as "quaternized sulfamic acid salts") have the following general formula: $R^1R^2R^3N^+S(O)_2(OH)$ where $R^1$ and $R^2$ are as defined above and $R^3$ is, for example, a hydrogen or a $C_1$–$C_{20}$ alkyl group, such as discussed above.

The methods according to the invention may be part of an overall water treatment regimen. The sulfamic acid or salt thereof may be used with other water treatment chemicals, particularly with biocides (e.g., algicides, fungicides, bactericides, molluscicides, oxidizers, etc.), stain removers, clarifiers, flocculants, coagulants, or other chemicals commonly used in water treatment. For example, submergible surfaces may be contacted with a sulfamic acid or salt thereof as a pretreatment to inhibit bacterial adhesion and placed in aqueous system using a microbicide to control the growth of microorganisms. Or, an aqueous system experiencing heavy biological fouling may first be treated with an appropriate biocide to overcome the existing fouling. A sulfamic acid or salt thereof may then be employed to maintain the aqueous system. Alternatively, a sulfamic acid or salt thereof may be used in combination with a biocide to inhibit bacteria from adhering to submerged surfaces within the aqueous system while the biocide acts to control the growth of microorganisms in the aqueous system. Such a combination generally allows less microbicide to be used.

"Controlling the growth of the microorganisms" in an aqueous system means control to, at, or below a desired level and for a desired period of time for the particular system. This can be eliminating the microorganisms or preventing their growth in the aqueous systems.

The sulfamic acid or salt thereof may be used in the methods of the invention as a solid or liquid formulation. Accordingly, the present invention also relates to a composition containing a sulfamic acid or salt thereof. The composition comprises at least one sulfamic acid or salt thereof in an amount effective to inhibit bacteria from adhering to a submergible surface or a submerged surface within an aqueous system. When used in combination with another water treatment chemical such as a biocide, the composition may also contain that chemical. If formulated together, the sulfamic acid or salt thereof and water treatment chemical should not undergo adverse interactions that would reduce or eliminate their efficacy in the aqueous system. Separate formulations are preferred where adverse interactions may occur.

Depending on its use, a composition according to the present invention may be prepared in various forms known in the art. For example, the composition may be prepared in liquid form as a solution, dispersion, emulsion, suspension, or paste; a dispersion, suspension, or paste in a non-solvent; or as a solution by dissolving the sulfamic acid or salt thereof in a solvent or combination of solvents. Suitable solvents include, but are not limited to, acetone, glycols, alcohols, ethers, or other water-dispersible solvents. Aqueous formulations are preferred.

The composition may be prepared as a liquid concentrate for dilution prior to its intended use. Common additives such as surfactants, emulsifiers, dispersants, and the like may be used as known in the art to increase the solubility of the sulfamic acid or its salt as well as other components in a liquid composition or system, such as an aqueous composition or system. In many cases, the composition of the invention may be solubilized by simple agitation. Dyes or fragrances may also be added for appropriate applications such as toilet waters.

A composition of the present invention may also be prepared in solid form. For example, the sulfamic acid or salt thereof may be formulated as a powder or tablet using means known in the art. The tablets may contain a variety of excipient known in the tableting art such as dyes or other coloring agents, and perfumes or fragrances. Other components known in the art such as fillers, binders, glidants, lubricants, or antiadherents may also be included. These latter components may be included to improve tablet properties and/or the tableting process.

The following illustrative examples are given to disclose the nature of the invention more clearly. It is to be understood, however, that the invention is not limited to the specific conditions or details set forth in those examples.

EXAMPLE 1
General Synthesis of a Sulfamic Acid:

Dissolved amine in dry solvent, such as THF, and chilled in an ice bath with stirring. Next chlorosulfonic acid was added such that the molar ratio of acid:amine is 1:1. After the reaction was complete, solvent was removed by means of rotary evaporation. The resulting sulfamic acid is then collected by filtration and dried.

EXAMPLE 2
Synthesis of Dodecyl Sulfamic Acid:

Dodecyl amine (0.1 mol) is added to a round bottom flask equipped with magnetic stirrer and dissolved in anhydrous pyridine. Next, chlorosulfonic acid (0.1 mol) is added dropwise with stirring to the chilled solution. The resulting product, dodecyl sulfamic acid, is then collected by filtration, washed with water and dried in an oven.

EXAMPLE 3

Test Method: The following method effectively defines the ability of a chemical compound to inhibit bacterial adhesion, or attack the formation of existing attached microorganisms, on various types of surfaces. As an overview, bioreactors were constructed in which approximately 1 in.×3 in. slides (glass or stainless steel) were fixed to the edge of the bioreactor. The lower ends (approx. 2 in.) of the slides dipped into a bacterial growth medium (pH 7) within the bioreactor which contained a known concentration of the test chemical. Following inoculation with known bacterial species, the test solutions were stirred continuously for 3 days. Unless otherwise indicated in the results below, the medium within the bioreactor was turbid by the end of three days. This turbidity indicated that the bacteria proliferated in the medium despite the presence of the chemical tested. This also shows that the chemical, at the concentration tested, showed substantially no biocide (bactericidal) activity. A staining procedure was then used on the slides in order to determine the amount of bacteria attached to the surfaces of the slides.

Construction of Bioreactors: The bioreactors comprised a 400 ml glass beaker over which a lid (cover from a standard 9 cm diameter glass petri dish) was placed. With the lid removed, slides of the material of choice were taped at one end with masking tape and suspended inside the bioreactor from the top edge of the beaker. This allows the slides to be submerged within the test medium. Typically, four slides (replicates) were uniformly spaced around the bioreactor. The score presented below are the average of the four replicates. A magnetic stirring bar was placed in the bottom of the unit, the lid positioned, and the bioreactor autoclaved. Two different types of material were used as slides, stainless steel as a metal and glass as a hydrophillic surface.

Bacterial Growth Medium: The liquid medium utilized in the bioreactors was described previously by Delaquis, et al., "Detachment Of Pseudomonas fluorescens From Biofilms On Glass Surfaces In Response To Nutrient Stress", Microbial Ecology 18:199–210, 1989. The composition of the medium was:

Glucose 1.0 g
$K_2HPO_4$ 5.2 g
$K_2PO_4$ 2.7 g
NaCl 2.0 g
$NH_4Cl$ 1.0 g
$MgSO_4.7H_2O$ 0.12 g
Trace Element 1.0 mL
Deionized $H_2O$ 1.0 L

TRACE ELEMENT SOLUTION:

$CaCl_2$ 1.5 g
$FeSO_4.7H_2O$ 1.0 g
$MnSO_4.2H_2O$ 0.35 g
$NaMoO_4$ 0.5 g
Deionized $H_2O$ 1.0 L The medium was autoclaved and then allowed to cool. If a sediment formed in the autoclaved medium, the medium was resuspended by shaking before use.

Preparation of Bacterial Inocula: Bacteria of the genera Bacillus, Flavobacterium, and Pseudomonas were isolated from a paper mill slime deposit and maintained in continuous culture. The test organisms were separately streaked onto plate count agar and incubated at 30° C. for 24 hours. With a sterile cotton swab, portions of the colonies were removed and suspended in sterile water. The suspensions were mixed very well and were adjusted to an optical density of 0.858 (Bacillus), 0.625 (Flavobacterium), and 0.775 (Pseudomonas) at 686 nm.

Biofilm Production/Chemical Testing: To four separate bioreactors was added 200 ml of the sterile medium prepared above. Chemicals to be evaluated as biodispersants were first prepared as a stock solution (40 mg/2 ml) using either water or a 9:1 acetone: methanol mixture (ac/MeOH) as a solvent. A 1.0 ml aliquot of the stock solution was added to the bioreactor using moderate, continuous magnetic stirring. This provided an initial concentration of 100 ppm for the test compound. One bioreactor (Control) contains no test compound. Aliquots (0.5 ml) from each of the three bacterial suspensions were then introduced into each bioreactor. The bioreactors were then provided with continuous stirring for three days to allow for an increase in bacterial population and deposition of cells onto the surfaces of the slides.

Evaluation of Results: The following compounds were evaluated using the procedure described above: butyl sulfamic acid, compound (a); amyl sulfamic acid, compound (b); octyl sulfamic acid, compound (c); dioctyl sulfamic acid, compound (d); dodecyl sulfamic acid, compound (e); didodecyl sulfamic acid, compound (f); dicyclohexyl sulfamic acid, compound (h); morpholino sulfamic acid, compound (i); and piperidinyl sulfamic acid, compound (j).

After the test was completed, the slides were removed from the bioreactors and were positioned vertically to permit air drying. The degree of adhesion of bacteria to the test surface was then estimated using a staining procedure. The slides were briefly flamed in order to fix the cells to the surface, and then transferred for two minutes to a container of Gram Crystal Violet (DIFCO Laboratories, Detroit, Mich.). The slides were gently rinsed under running tap water, and then carefully blotted. The degree of bacterial adhesion was then determined by visual examination and subjective scoring of each slide. The intensity of the stain is directly proportional to the amount of bacterial adhesion. The following biofilm scores are given:

0=essentially none  3=moderate
1=scant  4=heavy
2=slight

Chemical treatments were evaluated relative to the Control which typically receive an average score for the four bioreactor slides in the 3–4 range. Compounds which receive an average score in the 0–2 range were considered effective to prevent the adhesion of bacteria to the submerged slides. The results are shown in the following Table I:

TABLE I

| Compound | Solvent | Conc. (ppm) | MIC[1] pH6 | MIC[1] pH8 | Slides Glass or SS* | Score |
|---|---|---|---|---|---|---|
| a | Acetone | 100 | — | >500 | Glass | 1 |
| a | Acetone | 100 | — | >500 | Glass | 2 |
| a | Acetone | 100 | — | >500 | Glass | 2 |
| a | Acetone | 100 | — | >500 | Glass | 2 |
| b | Acetone | 100 | — | >500 | Glass | 1 |
| b | Acetone | 100 | — | >500 | Glass | 3 |
| b | Acetone | 100 | — | >500 | Glass | 3 |
| b | Acetone | 100 | — | >500 | Glass | 3 |
| c | Acetone | 100 | — | >100 | Glass | 1 |
| c | Acetone | 100 | — | >100 | Glass | 2 |
| c | Acetone | 100 | — | >100 | Glass | 2 |
| d | Acetone | 100 | — | >100 | Glass | 3 |
| e | Acetone | 100 | — | — | Glass | 3.8 |
| f | Acetone | 100 | — | — | Glass | 2.00 |
| h | Acetone | 100 | >500 | >100 | SS | 2.25 |
| h | Acetone | 100 | >500 | >100 | SS | 2.00 |
| i | Acetone | 100 | >500 | >100 | SS | 0.25 |
| i | Acetone | 100 | >500 | >100 | SS | 3 |
| j | Acetone | 100 | >100 | >100 | Glass | 2.5 |

[1]Minimum inhibitory concentration (MIC) for each compound against the bacteria E. Aerogenes using an 18 hour Basal Salts test at pH 6 and pH 8.
*SS = Stainless steel

EXAMPLE 4

The test method, construction of bioreactors, bacterial growth medium, preparation of bacterial inocula, and biofilm production/chemical testing is the same as outlined in EXAMPLE 3.

Evaluation of Results: The following compounds were evaluated using the procedure described above: butyl sulfamic acid, compound (a); amyl sulfamic acid, compound (b); octyl sulfamic acid, compound (c); dioctyl sulfamic acid, compound (d); dodecyl sulfamic acid, compound (e); didodecyl sulfamic acid, compound (f); octadecyl sulfamic acid, compound (g); dicyclohexyl sulfamic acid, compound (h); morpholino sulfamic acid, compound (i); and piperidinyl sulfamic acid, compound (j).

After 168 h (1 week) of incubation at 26–28 C, the slides were removed from the bioreactors and were positioned vertically to the test surface was evaluated using a staining procedure. The slides were briefly flamed in order to fix the cells to the surface, and then transferred for one minute to a container of Gram Crystal Violet (DIFCO Laboratories, Detroit, Mich.). The slides were gently rinsed under running tap water, carefully blotted, and again allowed to air dry overnight The degree of bacterial adhesion was then determined by a quantitative method of evaluation.

Quantitative Method of Evaluation of Bacterial Adhesion:

The pair of glass slides and the pair of stainless steel slides corresponding to each treatment were placed each in Petri plate with 10 mL ethanol (technical) to remove the crystal violet staining the cells attached to the slides. A 1 mL aliquot of the crystal violet ethanol solution obtained in each Petri plate was transferred each to a test tube with 9 mL of deionized sterile water (1/10 dilution). The blank for calibration of the optical instrument used for the evaluation was a solution of 1 mL of ethanol in 9 mL of deionized sterile water. The absorbance (ABS) of each solution was determined using a spectrophotometer (Spectronic 21, Bausch and Lomb) at a wavelength of 586 nm. The inhibition of bacterial adhesion (IBA) was calculated:

IBA=100 (ABS control−ABS treatment)\ABS control 90 or >% IBA=essentially no bacterial adhesion 89–70% IBA=scant 69–50% IBA=slight 30% IBA=moderate 29–<29% IBA=moderate Compounds which receive 50% IBA or greater were considered effective to prevent the adhesion of bacteria to the submerged slides. The results are shown in the following Table II.

TABLE II

| Compound | Solvent | Conc. (ppm) | MIC[1] pH6 | MIC[1] pH8 | Slides Glass SS* | Score (% IBA) 168 h Incub. |
|---|---|---|---|---|---|---|
| a | Acetone | 100 | — | >500 | Glass | 0 |
|   |         |     |   |      | SS* | 66 |
| b | Acetone | 100 | — | >500 | Glass | 65 |
|   |         |     |   |      | SS* | 14 |
| c | Acetone | 100 | — | >100 | Glass | 41 |
|   |         |     |   |      | SS* | 54 |
| d | Acetone | 100 | — | >100 | Glass | — |
|   |         |     |   |      | SS* | — |
| e | Acetone | 100 | — | — | Glass | 82 |
|   |         |     |   |   | SS* | 78 |
| e | Acetone | 100 | — | — | Glass | 72 |
|   |         |     |   |   | SS* | 70 |
| f | Acetone | 100 | — | — | Glass | 27 |
|   |         |     |   |   | SS* | 15 |
| g | Acetone | 100 | — | >500 | Glass | — |
|   |         |     |   |      | SS* | — |
| h | Acetone | 100 | >500 | >100 | Glass | 44 |
|   |         |     |      |      | SS* | 57 |
| i | Acetone | 100 | >500 | >100 | Glass | 47 |
|   |         |     |      |      | SS* | 39 |

TABLE II-continued

| Compound | Solvent | Conc. (ppm) | MIC[1] pH6 | MIC[1] pH8 | Slides Glass SS* | Score (% IBA) 168 h Incub. |
|---|---|---|---|---|---|---|
| j | Acetone | 100 | >100 | >100 | Glass | 40 |
|   |         |     |      |      | SS* | 68 |

[1]Minimum inhibitory concentration (MIC) for each compound against the bacteria E. Aerogenes using an 18 hour Basal Salts test at pH 6 and pH 8.
*Stainless Steel While particular embodiments of the invention have been described, it will be understood, of course, that the invention is not limited to those embodiments. Other modifications may be made. The appended claims are intended to cover any such modifications as fall within the true spirit and scope of the invention.

Deposit of Computer Program Listings

Not applicable

What is claimed is:

1. A composition for controlling biofouling of in an aqueous system, comprising
    at least one sulfamic acid or a salt thereof in an amount effective to inhibit bacteria from adhering to a submergible surface or a submerged surface within the aqueous system, wherein the sulfamic acid is a compound of the formula $R^1R^2NS(O)_2(OH)$, where $R^1$, $R^2$ are independently a hydrogen, a $C_4-C_{20}$ alkyl group or a cyclohexyl group, but $R^1$ and $R^2$ are not both hydrogen; or $R^1$ and $R^2$, together with the N, form a 5–8 membered heterocyclic ring having the formula:

in which X is O, NH, or $CH_2$; and wherein the salt of a sulfamic acid is an acid salt or a quaternized sulfamic acid salt.

2. A composition of claim 1, wherein
    $R^1$ is a $C_8-C_{18}$ alkyl and $R^2$ is a hydrogen.

3. A composition of claim 1, wherein
    $R^1$ and $R^2$ are each a $C_8-C_{18}$ alkyl group.

4. A composition of claim 1, wherein
    $R^1$ and $R^2$, together with the N, form said 5–8 membered heterocyclic.

5. A composition of claim 1, wherein
    the sulfamic acid is butyl sulfamic acid; amyl sulfamic acid; octyl sulfamic acid; dioctyl sulfamic acid; dodecyl sulfamic acid; didodecyl sulfamic acid; octadecyl sulfamic acid; dicyclohexyl sulfamic acid; morpholino sulfamic acid; piperidinyl sulfamic acid; or a mixture thereof.

6. A composition of claim 5, further comprising
    a biocide in an amount effective to control the growth of a microorganism in the aqueous system.

7. A composition of claim 1, wherein
    the composition is in liquid form.

8. A composition of claim 1, wherein
    the composition is in solid form.

9. The composition of claim 1, wherein the aqueous system is selected from the group consisting of an industrial aqueous system, a recreational aqueous system, and a sanitation aqueous system.

10. The composition of claim 9, wherein $R^1$ is a $C_8$–$C_{18}$ alkyl and $R^2$ is hydrogen.

11. The composition of claim 9, wherein $R^1$ and $R^2$ are each a $C_8$–$C_8$ alkyl group.

12. The composition of claim 9, wherein $R^1$ and $R^2$, together with the N, form said 5–8 membered heterocyclic ring.

13. The composition of claim 9, wherein the sulfamic acid is selected from the group consisting of butyl sulfamic acid, amyl sulfamic acid, octyl sulfamic acid, dioctyl sulfamic acid, dodecyl sulfamic acid, didodecyl sulfamic acid, octadecyl sulfamic acid, dicyclohexyl sulfamic acid, morpholino sulfamic acid, piperidinyl sulfamic acid, and mixtures thereof.

14. The composition of claim 13, further comprising a biocide in an amount effective to control the growth of a microorganism in the aqueous system.

15. The composition of claim 9, wherein at least one sulfamic acid or a salt thereof is in liquid form.

16. The composition of claim 9, wherein at least one sulfamic acid or a salt thereof is in solid form.

17. A composition in the form of a solution, dispersion, emulsion, suspension, paste, powder or tablet comprising at least one sulfamic acid or a salt thereof and at least one adjuvant selected from the group consisting of solvents, non-solvents, coloring agents, dyes, fillers, binders, fragrances, glidants, lubricants, antiadherents or biocides, wherein the sulfamic acid is a compound of the formula $R^1R^2NS(O)_2(OH)$, where $R^1$ and $R^2$ are independently a hydrogen, a $C_4$–$C_{20}$ alkyl group or a cyclohexyl group, but $R^1$ and $R^2$ are not both hydrogen; or $R^1$ and $R^2$, together with the N, form a 5–8 membered heterocyclic ring having the formula: in which X is O, NH, or $CH_2$; and wherein the salt of a sulfamic acid is an acid salt or a

in which X is O, NH, or $CH_2$; and wherein the salt of a sulfamic acid is an acid salt or a quaternized sulfamic acid salt, and the sulfamic acid or salt thereof is present in an amount effective to inhibit bacteria from adhering to a submergible surface or a submerged surface in an aqueous system to which the composition has been added.

* * * * *